United States Patent [19]
Comby et al.

[11] Patent Number: 5,265,619
[45] Date of Patent: Nov. 30, 1993

[54] PROCESS AND DEVICE FOR MEASURING VIBRATIONS, IN PARTICULAR NERVOUS TREMBLING IN LIVING ORGANISMS

[76] Inventors: Bruno Comby; Guy-Claude Burger, both of Chateau de Montramé, Soisy-Bouy, 77650 Longueville, France

[21] Appl. No.: 761,918
[22] PCT Filed: Apr. 4, 1990
[86] PCT No.: PCT/FR90/00232
§ 371 Date: Sep. 11, 1991
§ 102(e) Date: Sep. 11, 1991
[87] PCT Pub. No.: WO90/12293
PCT Pub. Date: Oct. 18, 1990

[30] Foreign Application Priority Data

Apr. 10, 1989 [FR] France .............................. 89/04674

[51] Int. Cl.⁵ .............................................. A61B 5/103
[52] U.S. Cl. .................................................... 128/782
[58] Field of Search ............... 128/782, 774, 739, 721, 128/670, 687, 689, 690; 73/579, 649, 652; 364/413.02, 413.05, 421

[56] References Cited

U.S. PATENT DOCUMENTS

| | | | |
|---|---|---|---|
| 1,664,210 | 3/1928 | Hall | 128/741 |
| 3,547,106 | 12/1970 | Bornmann | 128/721 |
| 3,797,010 | 3/1974 | Adler et al. | 128/782 |
| 4,010,637 | 3/1977 | Harwell et al. | 73/587 |
| 4,112,926 | 9/1978 | Schulman et al. | 128/782 |
| 4,117,834 | 10/1978 | McPartland et al. | 128/782 |
| 4,157,087 | 6/1979 | Miller et al. | 128/741 |
| 4,306,291 | 12/1981 | Zilm et al. | 364/508 |
| 4,550,603 | 11/1985 | Fukada et al. | 73/587 |
| 4,550,604 | 11/1985 | Sugimoto et al. | 73/587 |
| 4,870,868 | 10/1989 | Gastgeb et al. | 73/649 |
| 4,885,687 | 12/1989 | Carey | 364/413.02 |
| 4,926,863 | 5/1990 | Alt | 128/419 PG |
| 4,955,379 | 9/1990 | Hall | 128/633 |
| 5,025,791 | 6/1991 | Niwa | 128/670 |
| 5,031,614 | 7/1991 | Alt | 128/419 OPG |
| 5,067,488 | 12/1991 | Fukada et al. | 128/782 |
| 5,131,401 | 7/1992 | Westenskow et al. | 128/741 |
| 5,139,026 | 8/1992 | Niwa | 128/687 |
| 5,140,994 | 8/1992 | Campbell et al. | 128/782 |

FOREIGN PATENT DOCUMENTS

| | | | |
|---|---|---|---|
| 0087015 | 8/1983 | European Pat. Off. | |
| 2577791 | 8/1986 | France | |
| 1181631 | 9/1985 | U.S.S.R. | 128/782 |
| 2068127 | 8/1981 | United Kingdom | 128/782 |

OTHER PUBLICATIONS

Zilm et al. "The Nature and Etiology . . . Tremor" IEEE Transactions on Biomedical Engineering vol. BME-26, No. 1, Jan. 1979 pp. 3-10.
Colburn et al "An Ambulatory Activity Monitor . . . Memory" ISA Transactions: 15(1976) pp. 149-154.

*Primary Examiner*—Stephen C. Pellegrino
*Assistant Examiner*—Guy V. Tucker
*Attorney, Agent, or Firm*—Young & Thompson

[57] ABSTRACT

A process for measuring vibrations, especially nervous trembling in living organisms, and a device for implementing the process in disclosed. The device consists of a sensor which converts the vibrations into an electric signal processed by an electronic circuit making it possible to either display the result or to transmit the result to other apparatus. The different elements may or may not be contained within the same housing. The process and device serve essentially for measuring the degree of irritability and is for use by the general public, for medical checks on patients under supervision for neurological problems (Parkinson's disease, senile trembling, etc.) and for laboratory checks to measure trembling in living organisms in varied circumstances and especially after injection or ingestion of certain substances.

23 Claims, 9 Drawing Sheets

PROCESS AND DEVICE FOR MEASURING VIBRATIONS, IN PARTICULAR NERVOUS TREMBLING IN LIVING ORGANISMS

FIELD OF THE INVENTION

The present invention concerns a process for measuring vibrations and a device for implementing this process The vibrations measured can be those of an object, an animal or a person.

SUMMARY AND BACKGROUND OF THE INVENTION

The invention is characterized in particular by the fact that the vibrations of an object are measured by distinguishing phases of low-amplitude trembling of the object from phases of greater trembling due to unwanted stimulation, so as to respond to the lowest values (trembling when resting) and eliminate the highest values. One manner of distinguishing resting trembling phases from greater amplitude trembling phases due to unwanted stimulation consists in measuring the absolute minimum of the amplitude of vibrations of an object over a predetermined period. Thus a sudden and unexpected vibration during the measurement (twitch, impact, etc) has no effect on the result.

Applications of the invention to measuring the nervous trembling of living organisms are particularly useful because the amplitude of trembling when an animal or a person is resting increases when the animal or person is irritated, tired or has consumed unnatural substances (tobacco, coffee, artificial foodstuffs, etc). Simple measurement of the amplitude of trembling is insufficient, however, because the signal generated by the sensor is the result of microscopic trembling (which is of interest) and of macroscopic muscular movements of much greater amplitude. It is not possible to distinguish trembling when resting from trembling when active (or muscular trembling) by frequency-selective filtering, as resting trembling and muscular trembling are of the same frequency, in the order of 10 Hz in man. The process and the device in accordance with the invention have the advantage, whilst distinguishing clearly trembling of the body from greater amplitude trembling phases due to unwanted vibrations, of showing up only the resting trembling, movements of the animal during the measurement having no effect on the result.

Stress in man is traditionally measured by measuring body temperature or cardiac rhythm. These parameters give only an approximate indication of the degree of stress, however, and devices available to the general public, in particular those which measure the temperature of the fingers by means of substances responsive to temperature, are highly inaccurate.

The device in accordance with the invention quantifies stress objectively and accurately using a physiological parameter different from those used previously: it quantifies the trembling of the organism when resting, which is invisible or virtually invisible to the naked eye in man. Measuring vibration of the human organism as a stress indicator is new as far as the applicants are aware. The present invention has the advantage of giving a more accurate result than previous devices which is more closely related to the actual degree of stress. The possibility of measuring stress using the present invention results from the fact that a stress reaction is accompanied by the discharge of adrenalin which increases the amplitude of nervous trembling.

Experiments have shown that vibration as measured using the device in accordance with the present invention increases effectively in persons in a stressful situation and in persons who smoke tobacco or consume unnatural foodstuffs, the level of trembling being then three to five times higher than under normal conditions. The measurement results decrease over a few days in persons who stop smoking, drinking coffee and/or adopt a more natural dietary regime Trembling also decreases between the start and the end of a relaxation session, which confirms that the measured parameter is a good stress indicator and opens up the possibility of using the invention to evaluate the efficacy of anti-stress methods (relaxation, seawater therapy, etc). At present there is no known means of reliably measuring stress and consequently no means of measuring the effectiveness of these methods or of comparing them with each other, as is now made possible by the invention. The inventors' experiments have shown that the smallest amount of unnatural substance (nicotine, cafeine, foodstuffs rendered unnatural by cooking or irradiation, bread, etc) when introduced into a living organism increases almost immediately the vibration as measured by the device to be described, which makes it possible to detect even very small amounts of abnormal substances in foodstuffs.

Patent FR 2 577 791 discloses a process and a device for evaluating the psychotropic effects of medication substances in animals by measuring meaningful agitation of the animals. The sensors and signal processing techniques of the present invention are very different from those as previously described in this French patent, however. In particular, the principle of measuring trembling when resting (treatment of the signal to ignore any signals other than low-amplitude signals, for example by detecting a minimum, ignoring unwanted signals of greater amplitude) is previously unknown, the prior art processes measuring all meaningful agitation of an animal and not its activity when resting.

Patent EU 0 087 015 describes a device designed to alert a farmer that a cow or other livestock animal is about to give birth. The device described detects contractions of the uterus of the animal by means of a mercury sensor which closes above a particular contraction threshold. This process is totally different from the present invention because the present invention measures the amplitude of trembling when resting, whereas the patent EU 0 087 015 measures muscular contractions above a particular movement threshold. The signal processing is therefore totally different: in the present invention, the amplitude of trembling when resting is measured instead of the muscular activity above a particular threshold, the muscle signal being eliminated because it is regarded as unwanted interference. Also, the sensor of the patent 0 087 015 produces a binary (on/off) signal which is obviously processed in a very different way from the signal of the present invention, signal.

BRIEF DESCRIPTION OF THE DRAWINGS

The features and the advantages of the invention will emerge from the following description given by way of non-limiting example with reference to the appended drawings in which.

DETAILED DESCRIPTION OF THE INVENTION

The measurement of vibration may comprise the following operations (the letters relate to FIGS. 5 and 6):
conversion of the vibrations into an electrical signal by means of a piezo-electric sensor (a)—amplification by an amplifier circuit (b)—filtering by high-pass and low-pass filters—rectification by a full-wave rectifier circuit (c)—squaring by a quadratic circuit (d)—smoothing of the signal low-pass filter (e) detection of a minimum value (f)—display or transmission of the result to other equipment (g)

The first two high-pass and low-pass filters select a range of frequencies. To measure trembling in man, for example, the relevant frequency range is from about 3 Hz to about 20 Hz. By filtering out frequencies below 3 Hz and above 20 Hz, unwanted signals resulting from mechanical resonances (low frequencies) or induction from the AC line voltage (50 Hz), for example, are eliminated.

Figure 5:
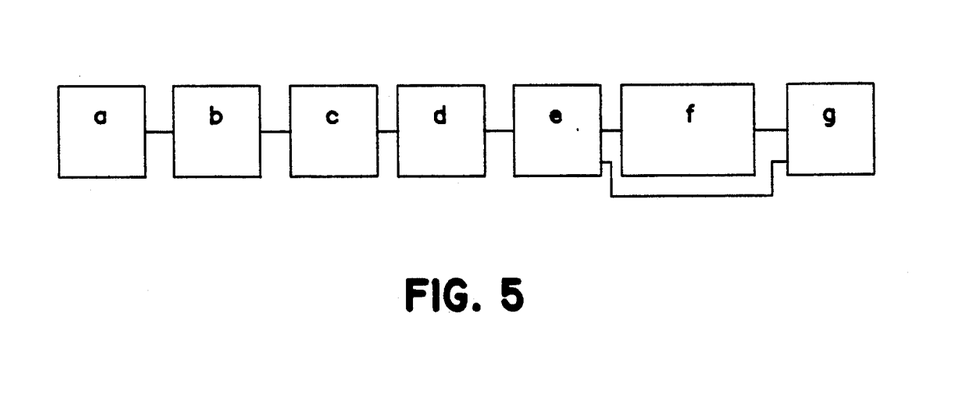
- FIG. 5 is a block diagram.

The electronic circuit for processing the signal supplied by the sensor can therefore comprise an amplifier circuit (b), a rectifier (c), filters and in particular a low-pass smoothing filter (e) and a minimum value detector (f). Optionally there may be added to these a frequency-selective corrector circuit and a squaring (quadratic) circuit (d).

There are various ways to eliminate unwanted signals representative of a high amplitude so as to retain only the trembling when resting. The absolute minimum signal level during the measurement may be measured, for example. It is also possible to measure the mean of the minimum values observed during the predetermined duration of the measurement or the number of times that the signal falls below a predetermined trembling threshold or the time for which the signal remains below a particular threshold, etc. The common feature of these various processes is that only the lowest vibration amplitudes are retained, higher values being eliminated because they are regarded as unwanted interference signals. Signal processing of this kind can obviously be combined with selective filtering of certain vibration frequencies.

The various component parts of the device in accordance with the invention: sensor, electronic circuit and display can be combined in a single unit, although this is not essential.

Figure 1:
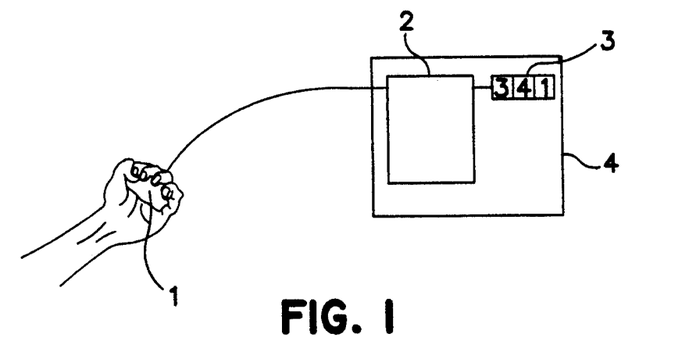
- FIGS. 1 and 2 are schematic illustrations of two embodiments of the invention.

FIG. 1 shows one embodiment of the device in accordance with the invention for consumer (stress measurement) and medical applications. The sensor (1) can be held in the hand, for example. It is connected to the rest of the equipment by an electrical cable that is preferably a screened (coaxial) cable and which conveys the electrical signal to the circuit (2). In this example, the equipment unit (4) contains both the circuit (2) and the display (3). The system can be battery-powered or mains-powered.

Figure 2:
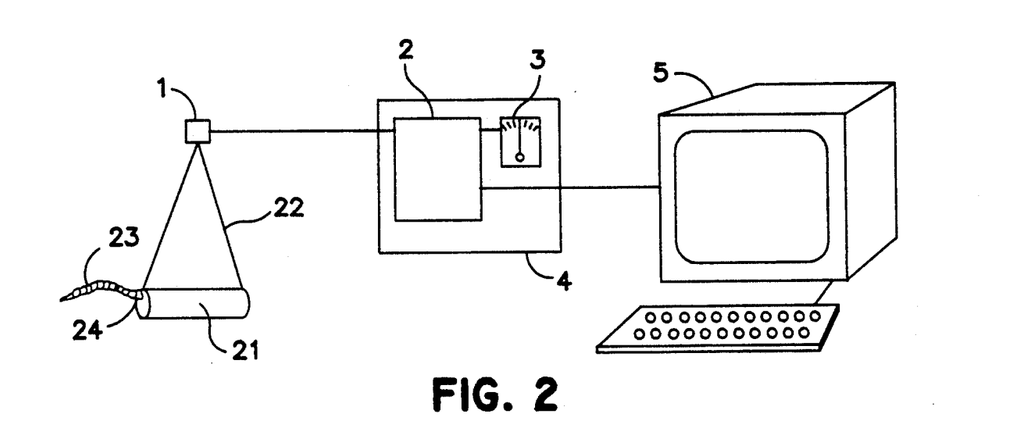

FIG. 2 shows another preferred embodiment more particularly intended for laboratory applications. The sensor (1) is, for example, attached to a cradle (21) containing a mouse or other animal (23) by means of a connecting device (22). The result can be transmitted to a computer or recording or printing system (5). The equipment unit (4) contains both the circuit (2) and the display (3) and is connected to the sensor (1) and to the peripheral devices (5).

Figure 3:
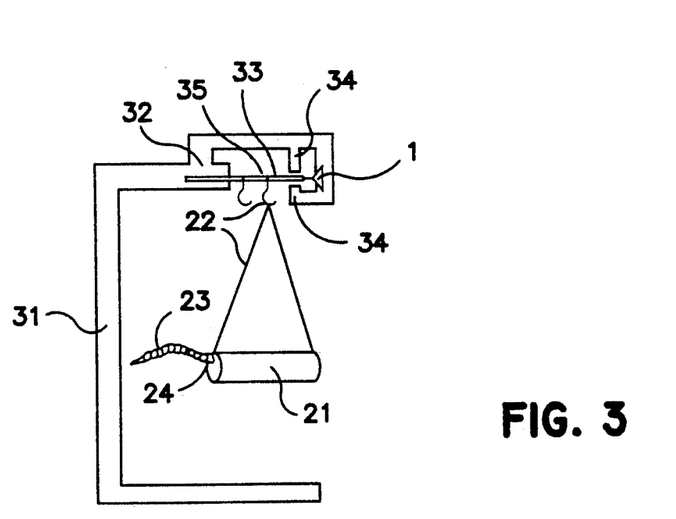
- FIG. 3 shows one example of sensors for measurements on animals.

FIG. 3 shows a sensor specifically designed for measuring vibration in rodents and comprising a piezo-electric cell (1) attached to a vibrating blade (33) connected to a fixed base (32) and by a connecting member (22) to the subject of the measurement (23), the travel of the blade being limited by abutments (34) which prevent damage to the blade in the event of abnormally high traction on the connecting member (22). The position at which the connecting member (22) and the blade (33) join can be adjusted. This has the advantage of making the sensitivity of the sensor adjustable. The same sensitivity would not be used to measure vibration of a mouse and vibration of a rat, for example. The coupling member (22) may be a suspension arrangement, using one or more wires, for example, or any other suspension system, the sensor being mounted on a column (31). The length of the suspension device (22) is calculated so that spontaneous oscillations of the cradle due to movements of the mouse (swinging movement) are filtered out by the circuit and do not corrupt the measurement result. If the object to be measured is an animal, one embodiment of the process in accordance with the invention places the animal in a cradle (21) the shape and size of which are such that the animal can enter the cradle but cannot turn round when inside it. This has the advantage of minimizing the movement of the animal in the cradle. Viewing means such as an orifice or window (24) provide an instantaneous indication of whether an animal (23) is present in the cradle or not.

Figure 4:
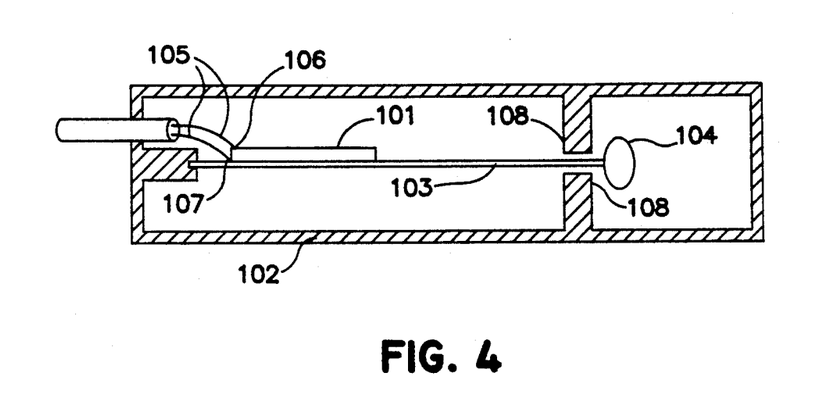
- FIG. 4 shows one example of a piezo-electric sensor very suitable for measurements on man.

FIG. 4 is a cross-section view of an acceleration sensor for implementing the invention that is easy to manufacture on an industrial scale at low cost. This sensor is specifically designed to be held in the hand to measure trembling in humans. It is based on a piezoelectric element such as a piezo-electric ceramic crystal (101) which produces between its opposite sides (106 and 107) a potential difference proportional to how much it is bent. The piezo-electric element is attached to an assembly that is mobile in bending, for example a flexible blade (103). One end of the mobile assembly (103) is attached to the sensor housing (102), for example by being embedded in it or bonded or welded to it; the other end carries a counterweight (104). Movements of the mobile assembly (103) relative to the casing (102) due to the inertia of the counterweight (104) excite the piezo-electric element (101). The system therefore operates as an acceleration sensor. The travel of the mobile assembly or the counterweight is limited by abutments (108) to avoid damage to the sensor in the event of sudden movement or impact. A sensor of this kind using a piezo-electric ceramic crystal bonded to a metal flexible blade produces an alternating current potential difference at the same frequency as the trembling and whose amplitude is proportional to the amplitude of the trembling, as is shown by the response curve reproduced in FIG. 8. The signal delivered by the sensor is transmitted to the circuit by two electrical wires (105) soldered to the faces (106 and 107) of the ceramic crystal. These wires (105) are sufficiently flexible not to impede the flexing of the ceramic crystal. For the same reason, it is advantageous to make the soldered connections (106 and 107) as small as possible and at the casing end of the ceramic crystal rather than at its center. A sensor of this kind is easy to manufacture on an industrial scale at low cost and is particularly suitable for implementing the invention. A variant of this sensor uses a strain gauge fixed to a flexible blade. An electrical contact at the abutments (108) can serve to advise the user, by appropriate display means such as a light-emitting diode, that the sensor is overloaded or damaged. Another type of sensor uses a gramophone cartridge with a counterweight added to the end of the stylus. Another sensor replaces the acceleration sensor with a piezo-electric element coupled directly or indirectly to the object being measured. The sensor for measuring trembling in man is preferably in contact with the hand of the subject or attached to another other part of the organism whose trembling is to be measured. The sensor can be unidirectional or multidirectional. To reduce the unit cost and facilitate signal processing it is preferable to use a unidirectional sensor. For measuring trembling in man, the sensor may be held in the hand, for example. So that the same physiological parameter is always measured, the position of the subject and how to hold the sensor during the measurement must be defined. The applicants have used the following standard position: the subject stands with the feet slightly apart, holding the sensor in the right hand (in the case of a right-handed person, or the left hand otherwise), gripping the sensor slightly, the arm virtually straight and held slightly away from the side. An asymmetric sensor, for example a sensor marked "top" and "bottom" or a sensor moulded with finger-shape imprints in the position in which it must be held makes it possible to impose the orientation of the sensor and therefore to be sure that the same component of trembling of the subject will always be measured. The electrical sensitivity of the sensor can be varied by a capacitor connected across the ceramic crystal or the piezoelectric cell. For a given force, the quantity Q of electricity delivered by the cell is constant: $Q = CV$, so that $V = Q/C$, in other words the voltage across the sensor is a function of C. The sensor may be housed in a small unit separate from the rest of the equipment, the signal being transmitted to the electronic circuit:
- either by an electrical wire,
- or by a radio transmitter device transmitting the signal from a transmitter in the sensor to a receiver in the electronic circuit.

FIG. 5 is a block diagram of the essential functions of the circuit from FIGS. 6A through 6G. The block a represents a piezo-electric sensor. The block b represents an amplifier. The block represents a rectifier. The block d represents a quadratic circuit. The block e represents a filter. The block f represents a circuit comprising a minimum value memory. The block g represents a display.

FIGS. 6A through 6G show an electronic circuit for implementing the invention; the major aspects of its operation will be explained hereinafter by way of example:

The letters through g in FIGS. 6A through 6G relate to the blocks in FIG. 5.

Figure 6A:
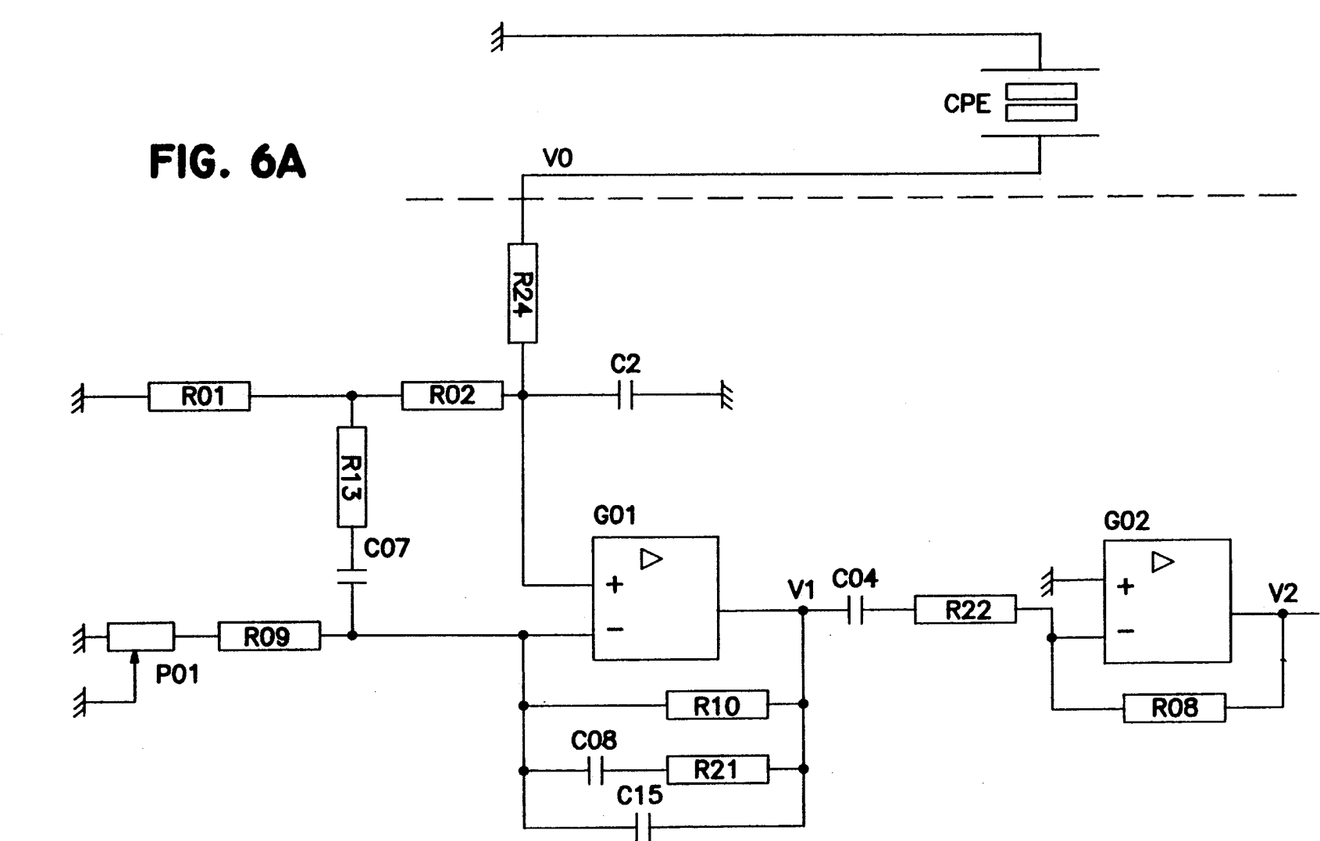
- FIGS. 6A through 6G constitute an electronic circuit diagram of one embodiment of the invention.

The circuit a in FIG. 6A shows the piezo-electric sensor CPE which produces an alternating current potential difference V0. It is a piezo-electric ceramic crystal whose impedance is equivalent to that of a 1 nF capacitor which, in parallel with C2 and with the input impedance of the amplifier G01, constitutes a high-pass filter with a cut-off frequency in the order of 1.5 Hz.

The amplifier-corrector circuit b in FIG. 6A comprises a first amplifier G01 whose gain is varied by P01. The input impedance is very high because of the feedback via C07 connected by R13 to the common point of R01 and R02. At very low frequencies the input impedance is R01+R02. The network comprising R10 in parallel with R21, C08 and C15 constitutes a $1/\sqrt{F}$ corrector network whose frequency attenuation is ten decibels per decade. The value of P01 is small in comparison with that of the corrector network. R10 is much higher than P01 which can produce a DC offset voltage at V1. A second amplifier G02 connected to V1 by R22 and C04 eliminates the offset voltage at V1. The positive input of the amplifier G02 is grounded. The negative input is connected to R08 whose other end is connected to the output V2 of G02 and to V1 by R22 and C04. The signal V2 is equal to the signal V0 modified by an amplification coefficient and corrected $1/\sqrt{F}$.

Figure 6B:
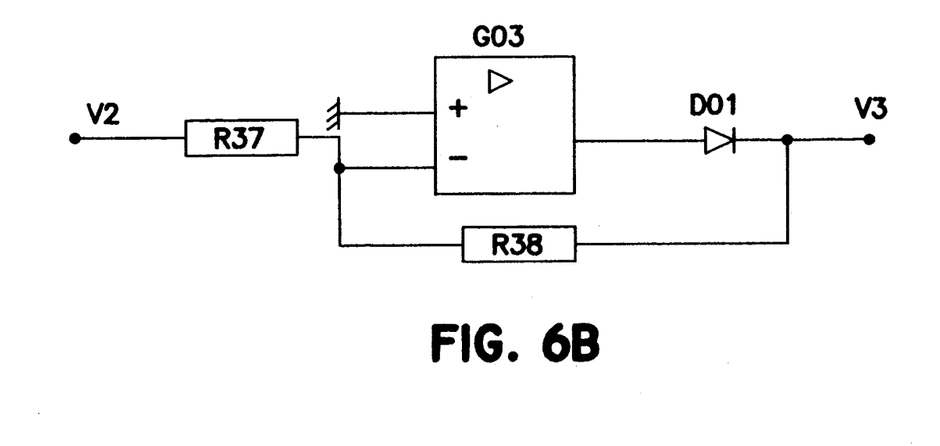

The circuit c in FIG. 6B is a full-wave rectifier comprising a diode D01, a rectifier amplifier G03 and two equal-value resistors R37 and R38. The signal V3 is therefore equal to the absolute value of the signal V2.

Figure 6C:
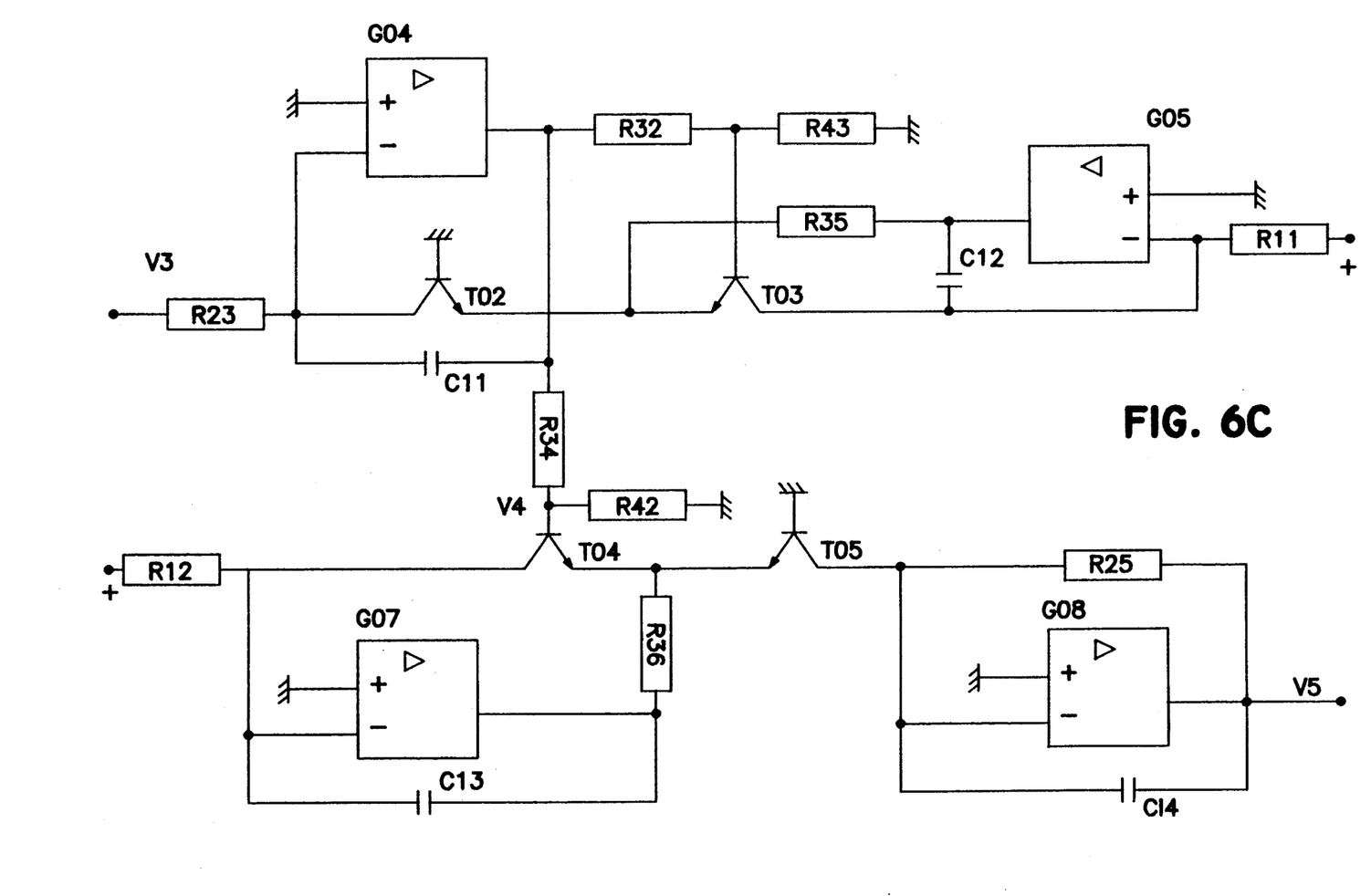

The circuit d in FIG. 6C squares the signal V3. This circuit is in two parts:
- the first part produces a voltage V4 proportional to the Naperian logarithm of the voltage V3,
- the second part delivers at V5 a voltage proportional to the exponential of V4.

An appropriate choice of the multiplier coefficient defined by the divider R34-R42 gives $V5 = (V3)^2$.

Figure 6D:
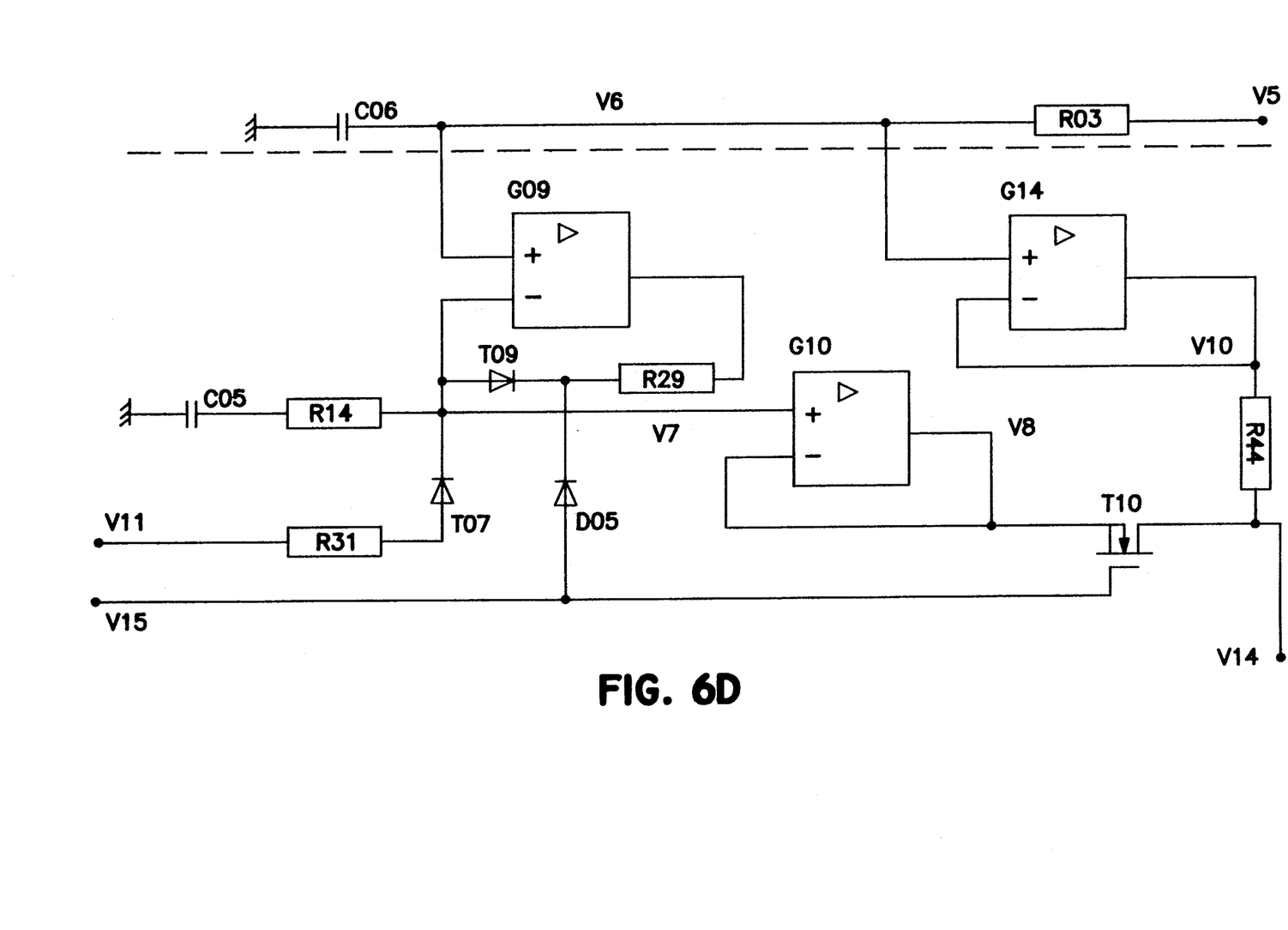

The function of the circuit in FIG. 6D is to smooth the rectified signal (by filtering out high frequencies), which is done by the low-pass filter R03-C06. The time constant is in the order of one to two seconds. This filtering prevents the minimum value detector circuit responding to any short-term interruption or reduction in trembling (in particular the zero crossing of each half-wave of a sinusoidal signal). The input of the filter is V5 and the output is V6, the common point of R03 and C06. The other terminal of C06 is grounded and the other terminal of R03 receives the signal V5 to be processed. The smoothed signal V6 is routed to the display by an impedance matching amplifier G14 and to a minimum value detector circuit.

The circuit f in FIG. 6D detects the absolute minimum value of the signal V6 since the start of measurement, this minimum value being stored in a storage capacitor C05 and given by the voltage at V7, the instantaneous value of the trembling being given by the voltage at V6 and V10. The start and the end of the measurement are determined by the control voltage V11 and the end of the measurement by the control voltage V15. The minimum value is detected by a minimum value detector amplifier G09 the positive terminal of which is connected to receive the instantaneous value of the signal V6, the negative input being connected via R14 to the storage capacitor C05. The output of the minimum value detector amplifier G09 is connected to its negative input and, via R29, to the cathode of a diode T09 whose anode is connected to C05 via R14, the other side of C05 being grounded. The point V7 representing the negative input of the minimum value detector amplifier G09, which contains the result of the minimum value measurement, routes the signal to the positive input of an impedance matching amplifier G10 of unity gain whose negative input is connected to its output at V8, the signal V8, equal to V7 but at a low impedance, being addressed to the display. The impedance matching amplifier G14 configured like G10 is designed to enable display of the signal V6 by producing the voltage V10 equal to V6 but at a low impedance. The VMOS switching transistor T10 connected to V8 and to V10 via R44 produces at V14 a voltage to be displayed equal to V8 or V10 according to the state of the control voltage V15. When it is turned off by a negative value at its control input V15, the switching transistor T10 produces at V14 the same voltage as V10, R44 being of much lower value than R15 (see R15 in FIG. 6E). If T10 is turned on by a positive value of its control voltage V15, the voltage V8 is reproduced at V14.

Figure 6E:
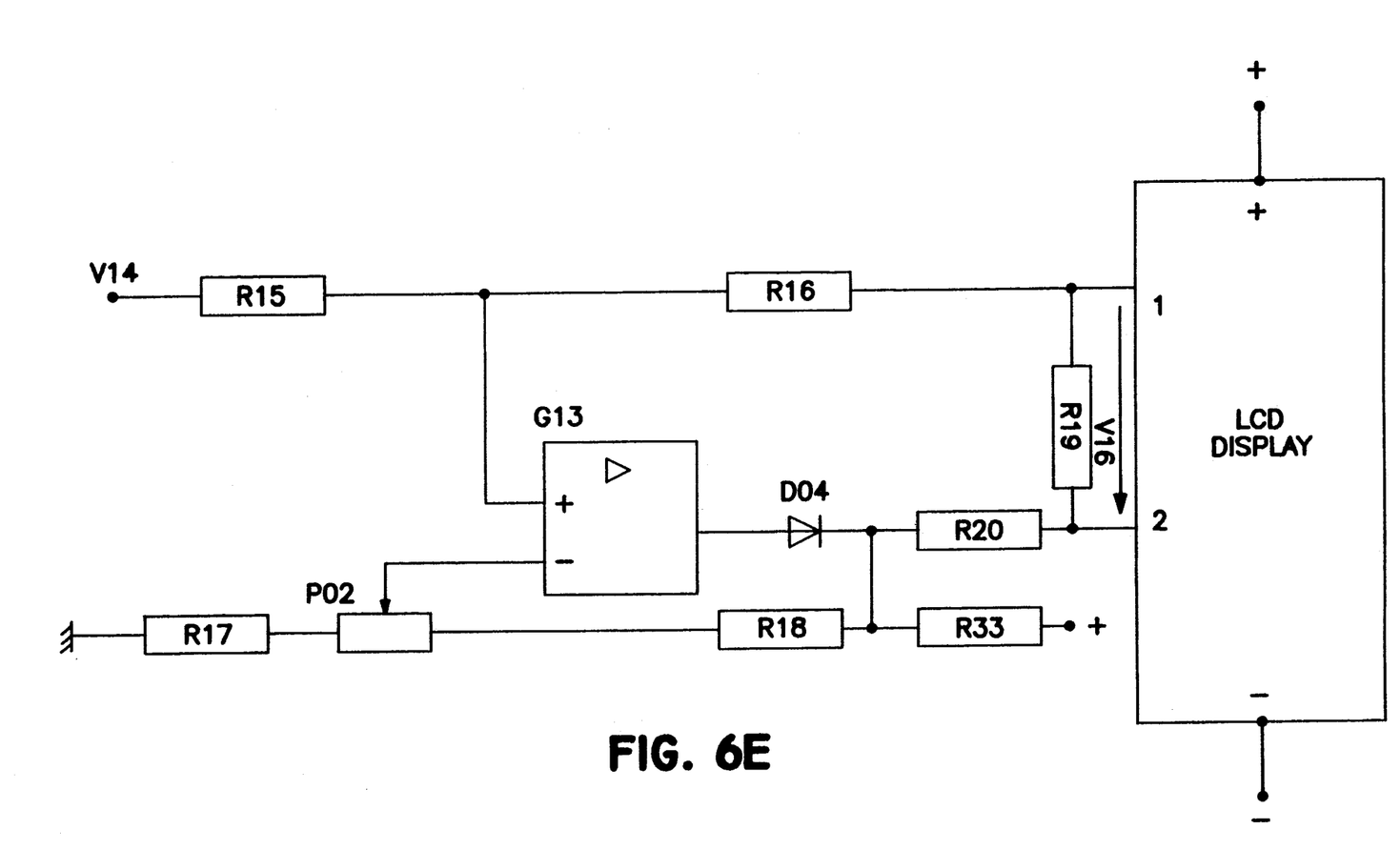

The circuit g in FIG. 6E displays the result of the measurement and/or the instantaneous value of the trembling on an LCD digital display. This circuit comprises on the input side of the display a differential amplifier G13 which transposes the voltage V14 into a voltage whose reference point is no longer ground but the input 1 of the display which is at an imposed voltage. The negative input of the differential amplifier G13 is connected to the center tap of a potentiometer P02 which adjusts the zero of the display in the absence of trembling. The voltage V16 displayed is therefore equal, during the measurement, to the instantaneous value of trembling and, after the measurement, to the absolute minimum value of the trembling during the measurement period.

Figure 6F:
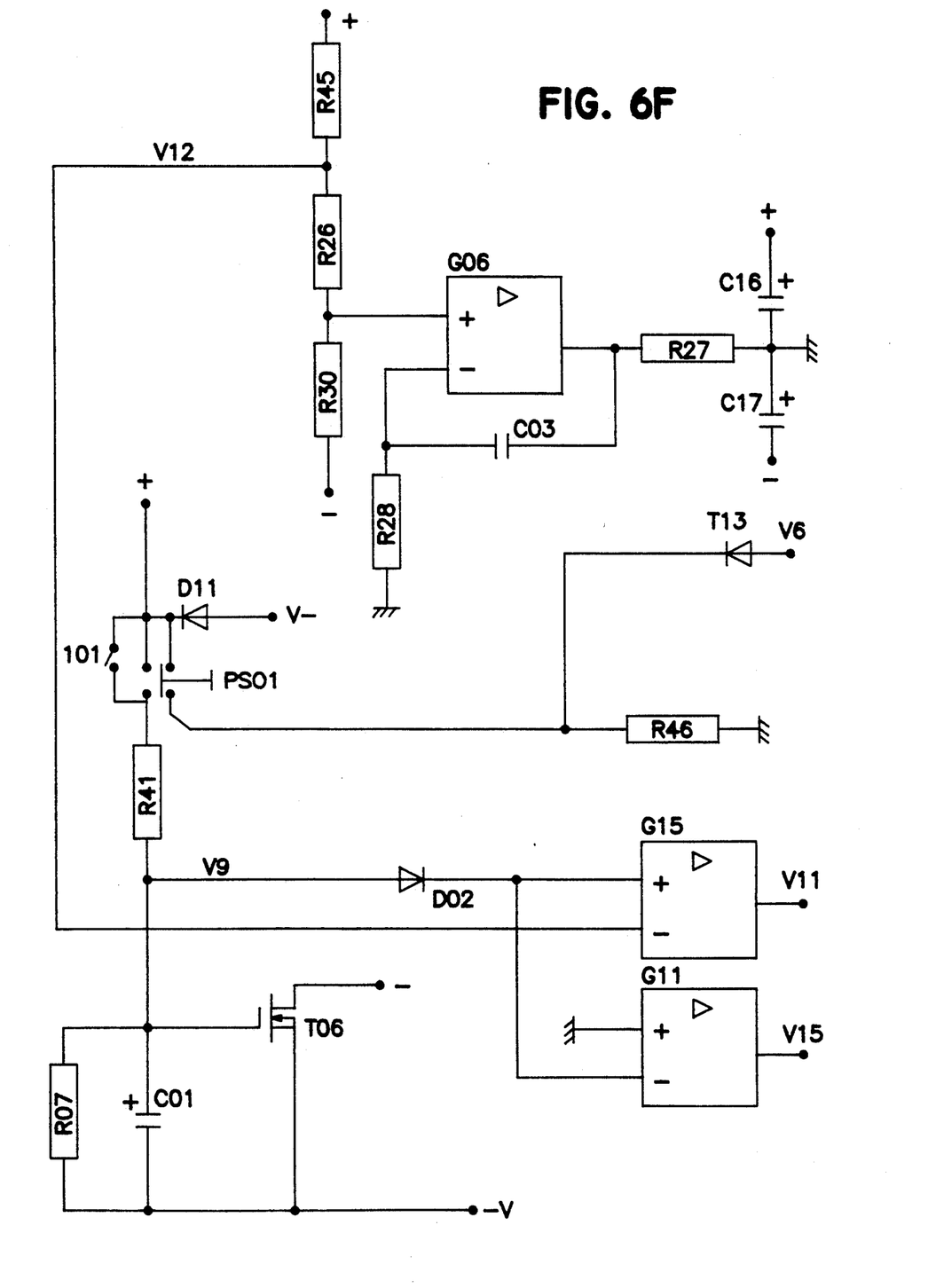

The circuit h in FIG. 6F is a control circuit. It comprises a switch-off transistor T06, a trigger device PS01, in this instance a pushbutton, which is operated to indicate the start of the measurement, a switch I01 which enables another use of the device, a time-delay circuit comprising a time-delay capacitor C01 discharging into a time-delay resistor R07, a control amplifier G15 which supplies a control voltage V11 and a control amplifier G11 which supplies a control voltage V15. The measurement is initiated by operating the pushbutton PS01 which initializes the time-delay C01-R07, which determines the duration of the measurement, by quickly charging the time-delay capacitor C01 through a resistor R41 and also initializes the storage capacitor C05 to a value greater than the expected measurement result by the control voltage V11 through R31 and T07. The time-delay C01-R07 imposes the following sequences:

- The equipment is switched on by operating the trigger unit PS01 which, by charging the time-delay capacitor C01 to a positive voltage through R41, activates the gate of the switch-on VMOS transistor T06 and turns it on, which energizes the (−) terminal of the circuit. Simultaneously, when the trigger unit PS01 is pressed, a voltage in the order of 0.3 Volt is imposed at V6 via T13. The control amplifier G15 delivers a positive voltage V11 which imposes via T07 a voltage at V7 equal to V6 equal to 0.3 Volt. While the trigger unit PS01 is activated, the control amplifier G11 delivers a negative control voltage V15 which causes the indicator diode DEL01 to blink on and off.

- Then, a few moments after the trigger unit PS01 is activated, the voltage V9 rises above the reference voltage V12 determined by the divider bridge R26-R45. The control amplifier G15 then delivers a positive control voltage V11 which at the start of the measurement initializes via T07 the storage capacitor C05 to a value V7 equal to the instantaneous value of the signal V6. Simultaneously, the control voltage V15 still causes the indicator diode DEL01 to blink on and off. As the control voltage V15 of the switching transistor T10 is still positive, the voltage displayed from activation of the pushbutton and throughout the duration of the measurement is equal to the instantaneous trembling value (V14=V10=V6). Likewise, when the switch I01 is closed, the voltage displayed is equal to the instantaneous trembling value V6 for as long as I01 remains closed. The equipment then operates as an instantaneous trembling value indicator.

- After a few seconds, when V9 reaches the threshold V12, the control voltage V11 becomes negative, which turns off the diode T07 and enables the minimum value detector. During the measurement, if the voltage V7 at the negative input of the minimum value detector amplifier G09 is greater than the trembling voltage V6 at the positive input, the output of the minimum value detector amplifier G09 forces its negative input to decrease. The obliges the charge on the storage capacitor C05 to be equal during the measurement to the minimum value reached by V6 since the start of the measurement.

When, at the end of the measurement, the voltage V9 drops below ground potential, the control voltage V15 becomes positive and via D05 imposes a positive voltage at the common point of T09-R29, which turns off the minimum value detector diode T09. Accordingly, V7 and V8 cannot reduce further, which is equivalent to latching the content of the storage capacitor C05. Simultaneously, the switching transistor T10 controlled by the control voltage V15 is turned on and the voltage displayed V14 is equal to V8, that is to say the absolute minimum value of the trembling during the measurement, which result is held in the storage capacitor C05. Simultaneously, the end of the measurement is signalled to the user by the display means DEL01 which is also conditioned by the time-delay C01-R07. When the control voltage V15 goes positive, the diode turned on which disables the oscillator of the circuit i (FIG. 6G).

- Still later, after the measurement result has been displayed for some time, and when the time-delay capacitor C01 has discharged sufficiently, the switch-on transistor T06 is turned off and the (−) terminal of the device is no longer energized. The equipment is then turned off automatically. When the switch I01 is closed, the time-delay capacitor C01 remains charged to the maximum charge, so that the equipment remains powered up continuously and displays the instantaneous trembling value.

Figure 6G:
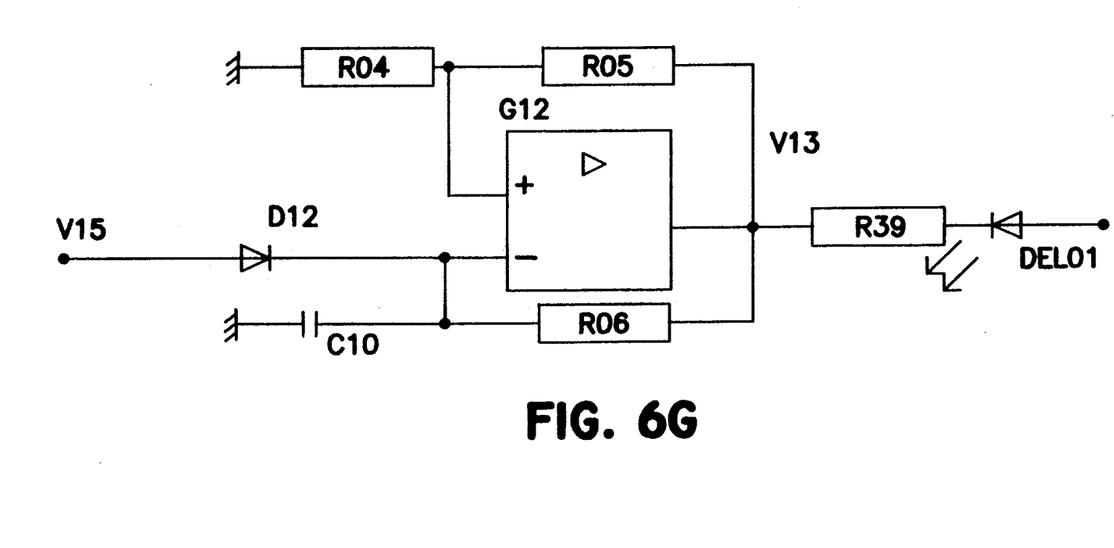

The circuit i in FIG. 6G is an oscillator controlling the signalling diode DEL01. The oscillator comprises an operational amplifier G12 controlled by the control voltage V15 through the diode D12. During the measurement the control voltage V15 is negative and the user knows that the measurement is in progress because the signalling diode DEL01 is blinking on and off. When the control voltage 15 goes positive at the end of the measurement, the diode D12 is turned on which disables the oscillator. The diode stops blinking on and off and the user is therefore advised of the end of the measurement.

Figure 7:
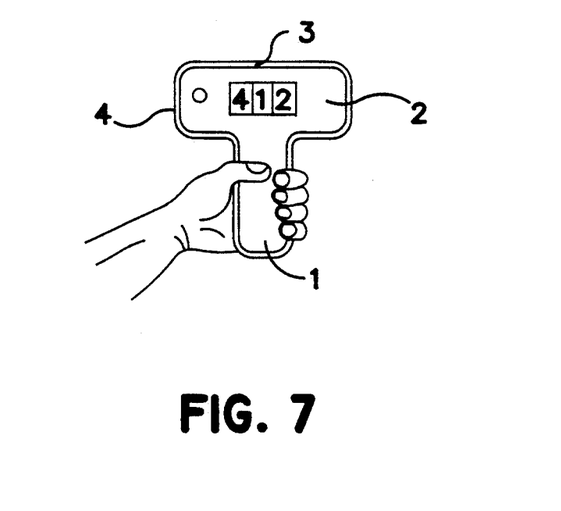
- FIG. 7 shows an embodiment of the invention with the sensor integrated into the equipment housing.

FIG. 7 shows a device combining the sensor (1), the circuit (2) and the display (3) in a common unit (4). This embodiment has the advantage of being less bulky and easier to use. The sensor can be an acceleration sensor situated inside the unit, for example, which is miniaturized and battery-powered so that it can be held in the hand or attached in some other way to the organism whose vibration is to be measured (fixed around the arm or the waist or the head by means of a strap, for example). This embodiment is particularly suited to measuring stress in man.

Figure 8:
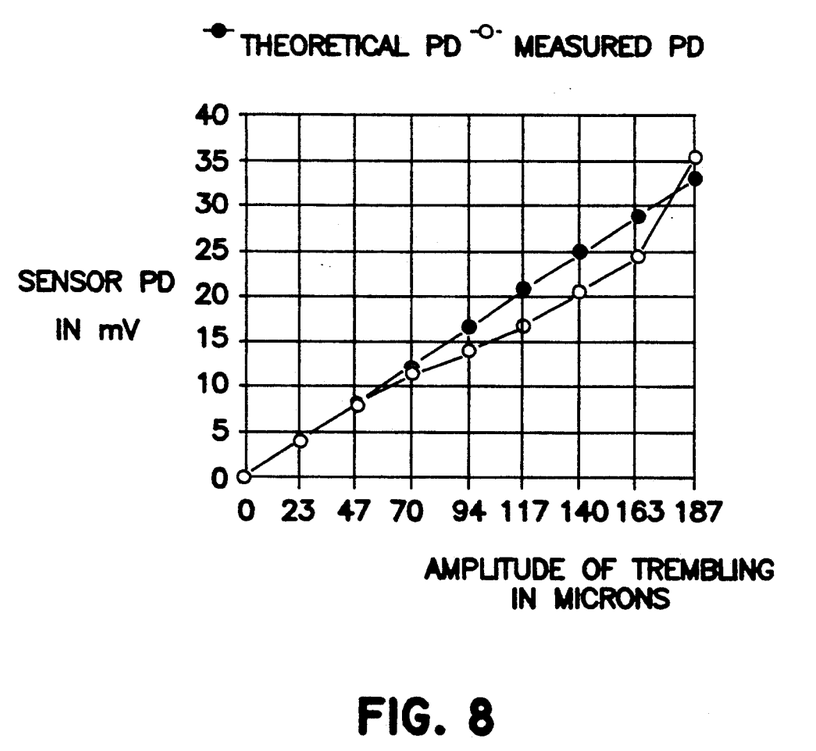
- FIG. 8 shows the response curve of the sensor from FIG. 4.

FIG. 8 shows the amplitude response curve of the sensor shown in FIG. 4. This curve is quasi-linear for frequencies in the order of 10 Hz, which makes a sensor of this kind ideal for measuring human trembling. As already explained, measurement of trembling requires a memory C05 to store the minimum trembling since the start of the measurement. One way to enable measurement of vibration during a predetermined time T when the measurement result is stored in the memory C05 is to start the measurement by means of a trigger unit, for example the pushbutton PS01, operation of which:
  - resets a time-delay C01-R07 determining the duration of the measurement, which may be variable,
  - initializes the memory C05 that will contain the result of the measurement.

If the absolute minimum level of vibration is measured during the measurement period, C05 is initialized by the trigger unit to a value higher than the expected measurement result.

It is known that the power dissipated by a vibrating object is proportional to the square of the vibration amplitude. Squaring the signal by means of the circuit d from FIGS. 5 and 6C enables an acceleration sensor to be used to generate a displayed signal proportional to the power dissipated in the form of vibrations. Squaring also has the advantage of increasing the spread of the measurement results.

The duration of the measurement must be chosen so that the object being measured achieves its basic level of trembling at least once during the measurement. Experiments have shown that a duration between five seconds and five minutes is perfectly suitable, the optimum duration for measurements in man being in the order of 20 seconds and in a mouse in the order of five minutes.

The signal reaching V5 has been amplified, corrected, rectified and squared. With a 15 Hz sinusoidal input signal, for example, the signal at V5 crosses zero every 1/30 second, however. Direct detection of the absolute minimum during a time interval in the order of one minute would therefore always yield a zero result if there were no smoothing (circuit e in FIG. 6D). The smoothing time constant is optionally variable by changing the values of C06 and R03. This facility finds particular application in laboratory uses where it is desirable to be able to process the signal differently by varying the smoothing time constant. At the end of the measurement the result is displayed for a time sufficient to be read, for example until the next measurement or until the equipment is powered off. In the device shown in FIGS. 6A-6G the measurement duration is in the order of 20 seconds and the result remains displayed for around 20 seconds at the end of the measurement, after which the equipment is switched off automatically.

In the FIGS. 6A-6G device the diode DEL01 blinks on and off during the measurement, is off when the equipment is off and is on when the result is displayed, enabling the user to distinguish readily between the three possible states of the equipment: measurement in progress, measurement completed and equipment off. Also, a diode blinking on and off during the measurement provides a focus for the attention of the subject, so that the equipment is more agreeable to use, the subject's concentration is improved and unwanted muscle movements are reduced.

The measurement duration T can be varied, for example, by substituting a potentiometer for R07. This finds an application in laboratory equipment where the measurement duration is variable depending on the animal used, the nature of the measurements to be performed, etc.

The potentiometer P01 is used to calibrate the equipment on completion of the manufacturing cycle or to try out measurements with variable gain, which find a specific application in laboratory uses where different kinds of measurement are required to be carried out using the same equipment: for example, because it is required to use different sensors on the same equipment or to allow for a correction factor or if it is required to calibrate the equipment prior to a series of measurements.

The device can display the instantaneous trembling value or the content of the memory C05 or other digits during the measurement. The display of the instantaneous trembling value during the measurement has the advantage for the user of enabling him to track changes in trembling as a function of movement, psychic condition, depth of meditation, etc. The device can therefore be used in a biofeedback technique whereby the user learns not to tremble because he can instantly see his trembling increase or decrease with his reactions. The device in accordance with the invention therefore finds applications in the rehabilitation of persons suffering from trembling (elderly persons, sufferers from Parkinson's disease alcoholics, etc).

The FIGS. 6A-6G device can also be used as a trembling indicator over a period longer than the specific duration of a measurement, for example by closing the switch 101. A device of this kind therefore has two functions: minimum trembling indicator over a predetermined period or instantaneous trembling indicator over an indeterminate period.

The device for implementing the invention can be miniaturized through the use of a microprocessor. It is even feasible to envisage the manufacture of wristwatches which indicate not only the time but also the degree of trembling (or the level of stress) using a miniaturized acceleration sensor. Miniature sensors of this type are already used at this time, in particular for various military applications. The use of a microprocessor makes it a simple matter to reduce the size of the circuit and of the display to fit into a wristwatch.

It is also possible to implement a hybrid device for measuring various physiological parameters, for example: cardiac rhythm, arterial blood pressure and nervous trembling. A unit and a display common to the three functions could be connected to an arm-strap fitted with an accelerometer to measure the nervous trembling of the arm and a pressure sensor to measure the arterial blood pressure and the cardiac rhythm.

The invention is not limited to the detailed embodiments described above by way of illustration only. Without departing from the scope of the invention it is possible to envisage other devices and other embodiments than those described, in particular using an electronic circuit comprising one or more microprocessors.

The invention is particularly intended for the following applications (this list is not limiting on the invention):

1) Consumer device for measuring trembling and stress in man, for example using an acceleration sensor held in the hand or integrated into the unit, which is miniaturized so that the entire device can be held in the hand.

2) Consumer or medical device for monitoring changes in microscopic trembling on giving up tobacco, on giving up coffee, on changing towards a more natural dietary regime (raw foods), during a thermal cure, during a relaxation session, etc.

3) Medical device for monitoring changes in trembling in patients affected by pathological trembling (Parkinson's disease, senility, giving up alcohol, stress, etc) or in persons being treated with drugs affecting the nervous system (sleeping pills, barbiturates, tranquilizers, anti-depressants, etc).

4) Laboratory device for measuring microscopic trembling in man, in mice and in other living organisms following injection or ingestion of various substances (pharmacological experiments, effects of various foodstuffs, etc).

5) Laboratory device for detecting irradiated foods (there is currently no measurement technique available for determining if a food has been irradiated or not). The principle is as follows: animals fed on 100% natural foodstuffs (natural and raw foods) are very sensitive to any unnatural processing of foodstuffs. The ingestion of artificial substances or irradiated foodstuffs causes pathological trembling in such animals which is invisible to the naked eye but can be measured. Mice can be used, for example. Any treatment of the foodstuffs by a process that does not exist in nature and which leads to even minimal modification of the molecular structure of the food (as with irradiation), causes a variation in the microscopic trembling of the animal in the hours or days following absorption. The following method can be used, for example: separate a batch of mice which have been fed 100% natural foodstuffs for sufficient time into two identical groups A and B. Group A is fed the foodstuffs under test (for example, potatoes which may or may not have been irradiated) and the control group B is fed with the same non-irradiated and untreated foodstuffs (organic potatoes in this example). If the potatoes have been irradiated, a modification of the microscopic trembling will be observed in the mice of group A as compared with those of group B. Lacking any absolutely identical but 100% natural foodstuffs for group B, other foodstuffs could be used provided that they are 100% natural. The animals would eat only this food for several days, during which their microscopic trembling is measured. More generally, note that the device in accordance with the invention can be used with a protocol of this type to detect the presence of neurologically active substances in foods (meat from animals treated with drugs or which have ingested unnatural substances, foodstuffs heated to above natural temperatures (around 40° C.), food additives, chemical treatment before or after harvesting, etc).

6) Device for measuring stress in car drivers, aircraft pilots, racing car drivers, etc.

7) Device for measuring reaction times in stress situations for training and/or screening of astronauts, aircraft pilots, business managers, drivers or candidates for any other post requiring good stress management.

8) Device for developing and monitoring the effectiveness of anti-stress methods (relaxation, meditation, seawater therapy, exercise, etc).

9) Monitoring stress in prisoners, for example to avoid releasing a prisoner who is still too stressed.

10) Measuring nervous trembling as a means of detecting lying during criminal investigations.

11) Miniaturized consumer device for measuring stress, for example a wristwatch which indicates the time and also the degree of stress, which could be accumulated over a particular period, for example one day.

12) Measuring vibration of objects other than living organisms, for example dwellings, automobile bodies, aircraft fuselages, trains, rockets, seismic measurements, etc.

We claim:

1. Method for detecting and processing vibrations of a person to be tested comprising the steps of: detecting low frequency vibrations of the body of the person in the range from about 3 Hz to about 20 Hz, converting the detected vibrations into a signal having a corresponding frequency and amplitude, processing the signal including rectifying and smoothing the same, so as to eliminate values above a threshold level of amplitude and determine the absolute minimum value of the rectified and smoothed signal for the detection period.

2. Method according to claim 1, wherein the low frequency detection is effected non-invasively by applying a vibration detection means to the body.

3. Method according to claim 1, wherein the detection of low frequency amplitude values is carried out over a period of time between 5 and 20 seconds.

4. Method according to claim 1, wherein the minimum value is displayed upon completion of the low frequency vibration detection period.

5. Method according to claim 4, wherein the completion of the detection of the low frequency vibration period is displayed so as to be viewed by the person to be tested.

6. Method according to claim 1, wherein the person to be tested initiates the low frequency vibration detection period.

7. Method according to claim 1, wherein the minimum value is stored or recorded.

8. Method according to claim 1, wherein the step of processing the signal includes filtering out frequencies below about 3 Hz and above about 20 Hz.

9. Method for detecting and processing vibrations of a person to be tested comprising the steps of: detecting low frequency vibrations of the body of the person, converting the detected vibrations into a signal having a corresponding frequency and amplitude, and processing the signal including rectifying and smoothing so as to eliminate values of the amplitude above a threshold level of amplitude, said detecting step comprising detecting the low frequency vibrations inside a closed hand of the person to be tested.

10. Method according to claim 9, wherein the person to be tested is in a standing position, his/her feet slightly apart, and his/her arms hanging slightly away from his/her body during the detection of the low frequency vibrations.

11. Apparatus for detecting and processing vibrations of a person to be tested comprising means for detecting low frequency vibrations, adapted to be applied to the body of the person, means for converting the detected vibrations into a signal having a corresponding frequency and amplitude, and means for processing the signal including rectification and smoothing, and means defining the low frequency vibration detection period of the order of 20 seconds connected to the processing means so as to determine the absolute minimum amplitude value during the low frequency vibration detection period.

12. Apparatus according to claim 11, wherein the means for detecting the low frequency vibrations is adapted to be held in the hand of the person to be tested.

13. Apparatus according to claim 12, wherein the means for detecting the low frequency vibrations has opposed ends and means for indicating the correct orientation in the hand of the person to be tested.

14. Apparatus according to claim 11, further comprising means for displaying the minimum value processed by the processing means, responsive to the completion of the low frequency detection period.

15. Apparatus according to claim 11, wherein the processing means comprises means for filtering out frequencies below about 3 Hz and above about 20 Hz.

16. Apparatus according to claim 11, wherein the means for detecting the low frequency vibrations comprises an acceleration sensor means having a flexible member responsive to low frequency vibrations of the body of the person to be tested and a piezo-electric member detecting a potential difference between opposite sides of said flexible member, and wherein said flexible member comprises a flexible blade attached at one end to a housing and carrying a flyweight at a location remote from said one end.

17. Apparatus according to claim 16, further comprising opposed abutments proximate to the flyweight for limiting movements of the flexible blade in order to prevent damage due to shocks or high amplitude movements.

18. Apparatus according to claim 11, wherein said means for processing the signal comprises amplifier means, filtering means, smoothing means and means for storing the absolute minimum value of the signal.

19. Apparatus according to claim 18, further comprising means for displaying the absolute minimum value.

20. Apparatus according to claim 11, further comprising means for starting the low frequency vibration detection period actuable by the person to be tested.

21. Apparatus according to claim 20, further comprising means for displaying the end of said low frequency vibration detection period, said means for displaying being visible by the person to be tested.

22. Apparatus according to claim 11, wherein said means for processing further comprises a memory for storing absolute minimum values of amplitude from the start of low frequency vibration detection period.

23. Apparatus according to claim 11, further comprising means for displaying a value of representative of the low frequency vibrations for viewing by the person to be tested thereby enabling the person to follow increases and decreases in trembling as a function of the persons' reactions.

* * * * *